US008532259B2

(12) United States Patent
Shedlock et al.

(10) Patent No.: US 8,532,259 B2
(45) Date of Patent: Sep. 10, 2013

(54) METHOD AND APPARATUS FOR COMPUTED IMAGING BACKSCATTER RADIOGRAPHY

(75) Inventors: Daniel Shedlock, Oak Ridge, TN (US); Christopher Meng, Gainesville, FL (US); Nissia Sabri, Gainesville, FL (US); Edward T. Dugan, Gainesville, FL (US); Alan M. Jacobs, Gainesville, FL (US); Sharon Auerbach Jacobs, legal representative, Gainesville, FL (US)

(73) Assignees: University of Florida Research Foundation, Inc., Gainesville, FL (US); Nucsafe, inc., Oak Ridge, TN (US)

( * ) Notice: Subject to any disclaimer, the term of this patent is extended or adjusted under 35 U.S.C. 154(b) by 160 days.

(21) Appl. No.: 12/812,427

(22) PCT Filed: Apr. 17, 2009

(86) PCT No.: PCT/US2009/041007
§ 371 (c)(1),
(2), (4) Date: Sep. 30, 2010

(87) PCT Pub. No.: WO2009/129488
PCT Pub. Date: Oct. 22, 2009

(65) Prior Publication Data
US 2011/0200172 A1   Aug. 18, 2011

Related U.S. Application Data

(60) Provisional application No. 61/045,823, filed on Apr. 17, 2008.

(51) Int. Cl.
*G01N 23/203* (2006.01)

(52) U.S. Cl.
USPC .............................................. 378/87

(58) Field of Classification Search
USPC .................................... 378/86–89
See application file for complete search history.

(56) References Cited

U.S. PATENT DOCUMENTS

| 6,122,344 A | 9/2000 | Beevor |
| 6,151,381 A | 11/2000 | Grodzins et al. |
| 6,269,142 B1 | 7/2001 | Smith |
| 6,876,719 B2 | 4/2005 | Ozaki |
| 6,879,657 B2 | 4/2005 | Hoffman |
| 7,072,440 B2 | 7/2006 | Mario et al. |
| 7,103,137 B2 | 9/2006 | Seppi et al. |

(Continued)

FOREIGN PATENT DOCUMENTS

| JP | 2006-519647 A | 8/2006 |
| WO | WO-2007-109227 | 9/2007 |
| WO | WO-2008-021807 A3 | 2/2008 |
| WO | WO-2009-129488 | 10/2009 |

OTHER PUBLICATIONS

Callerame, J., "X-Ray Backscatter Imaging: Photography Through Barriers," *Powder Diffraction*, Jun. 2006, vol. 21, No. 2, pp. 132-135.

(Continued)

*Primary Examiner* — Irakli Kiknadze
(74) *Attorney, Agent, or Firm* — Saliwanchik, Lloyd & Eisenschenk (57) ABSTRACT

Systems and methods of x-ray backscatter radiography are provided. A single-sided, non-destructive imaging technique utilizing x-ray radiation to image subsurface features is disclosed, capable of scanning a region using a fan beam aperture and gathering data using rotational motion.

48 Claims, 9 Drawing Sheets

(56) References Cited

U.S. PATENT DOCUMENTS

| | | |
|---|---|---|
| 7,162,005 B2 | 1/2007 | Bjorkholm |
| 7,203,276 B2 | 4/2007 | Arsenault et al. |
| 7,224,772 B2 | 5/2007 | Jacobs et al. |
| 7,545,910 B2 | 6/2009 | Harding et al. |
| 2001/0038680 A1 | 11/2001 | Davidson |
| 2002/0031202 A1 | 3/2002 | Callerame et al. |
| 2004/0240603 A1 | 12/2004 | Cai et al. |
| 2006/0133565 A1 | 6/2006 | Takagi et al. |
| 2006/0182217 A1 | 8/2006 | Harding et al. |
| 2007/0081624 A1 | 4/2007 | Nabatame |
| 2007/0153976 A1 | 7/2007 | Yokoyama et al. |
| 2007/0172026 A1 | 7/2007 | Schlomka et al. |
| 2007/0230657 A1 | 10/2007 | Garms |
| 2007/0280408 A1 | 12/2007 | Zhang |
| 2008/0219404 A1 | 9/2008 | Moore |

OTHER PUBLICATIONS

Carlsson, C.A., "Imaging Modalities in X-Ray Computerized Tomography and in Selected Volume Tomography," *Physics in Medicine and Biology*, Mar. 1999, vol. 44, No. 3, pp. R23-R56.

Defranould, P., "Acoustical Fan-Beam Measurements by Transducer Arrays for Tomography Reconstruction," *IEEE Transactions on Sonics and Ultrasonics*, Nov. 1981, vol. 28, No. 6, pp. 418-424.

Feng, Z., et al., "Depth Dependent Elastic Strain in ZnO Epilayer: Combined Rutherford Backscattering/Channeling and X-Ray Diffraction," *Nuclear Instruments & Methods in Phsyics Research, Section B*, Mar. 2005, vol. 229, No. 2, pp. 246-252.

Hupe, O., et al., "X-Ray Security Scanners for Personnel and Vehicle Control: Dose Quantities and Dose Values," *European Journal of Radiology*, Aug. 2007, vol. 63, No. 2, pp. 237-241.

Khettabi, F.E., et al., "A Nonrotating Multiparameter 3-D X-Ray Imaging System—Part I: Modeling and Reconstruction," *IEEE Transactions on Nuclear Science*, Jun. 2004, vol. 51, No. 3, pp. 641-647.

METHOD AND APPARATUS FOR COMPUTED IMAGING BACKSCATTER RADIOGRAPHY

CROSS-REFERENCE TO RELATED APPLICATIONS

This application is the U.S. national stage application of International Patent Application No. PCT/US2009/041007, filed Apr. 17, 2009, which claims the benefit of U.S. Provisional Application Ser. No. 61/045,823, filed Apr. 17, 2008, the disclosures of which are hereby incorporated by reference in their entireties, including any figures, tables, or drawings.

The subject invention was made with government support under a research project supported by the National Aeronautics and Space Administration (NASA) Grant No. NNM07AB25P. The government has certain rights to this invention.

BACKGROUND OF INVENTION

Figure 1A:
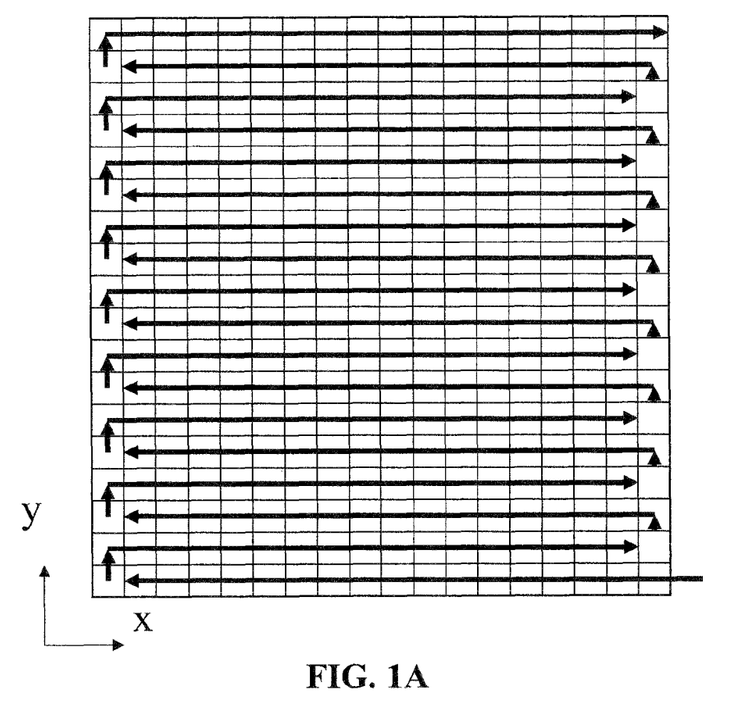
FIG. 1A shows the Radiography by Selective Detection (RSD) using pencil beam scanning.

X-ray backscatter imaging devices detect radiation coming back from a target. It is typically used for non-destructive examination applications where only one side of the target is available. The backscatter image can be used to "see" through walls or other barriers. The typical x-ray backscatter imaging utilizes Compton scattering. Compton scattering is a phenomenon of elastic scattering of photons and electrons. Compton x-ray backscatter images are formed by scanning a pencil-shaped beam and detecting the backscatter. A current backscatter technology primarily uses Radiography by Selective Detection (RSD) to generate images. RSD utilizes pencil beam Compton backscatter imaging that falls between highly collimated and uncollimated methods. Single and multiple scatters from the pencil x-ray beam are collected in detectors with collimators set to receive photons from below a plane determined by the desired scanning depth. Images are created by discretely collecting data over an area as the pencil beam rasters back and forth (FIG. 1A). RSD has the benefit of being faster than highly collimated techniques and providing better subsurface resolution than uncollimated methods.

BRIEF SUMMARY

Embodiments of the subject invention pertain to a method and apparatus for single-sided, non-destructive x-ray imaging. Additional embodiments relate to a method and apparatus for single-sided, non-destructive imaging using penetrating radiation such as gamma rays, neutrons, and electrons. Embodiments of the subject invention can be used for applications including, but not limited to, non-destructive examination, medical imaging, military, and security purposes. Embodiments of the invention can be referred to as computed imaging backscatter radiography (CIBR). Objects can be scanned with a fan beam of radiation having a length at least five times the width of the beam, where the object is scanned in a direction perpendicular to the length of the beam. The fan beam can be outputted from the radiation source, such as a tungsten target of an x-ray source, so that the radiation beam exits the radiation source as a fan beam. Embodiments can utilize a fan beam aperture. A beam of radiation can be passed through the fan beam aperture such that the output from the aperture is a fan beam of radiation. In addition, embodiments can gather data using rotational motion of the fan beam aperture. Embodiments of the present invention can increase scanning speed by illuminating a line instead of a spot and by using the fan beam to create a higher intensity backscatter field. In certain embodiments, the total amount of motion can be decreased by using back-projection or algebraic reconstruction to generate and interpolate the image.

BRIEF DESCRIPTION OF DRAWINGS

FIGS. 1A-1B show two methods of beam scanning, where

DETAILED DISCLOSURE

Embodiments of the present invention pertain to a method and apparatus for a single-sided, non-destructive imaging technique utilizing the penetrating power of x-ray radiation to image subsurface features. Embodiments can be referred to as Computed Imaging Backscatter Radiography (CIBR). Embodiments of the invention can be used for a variety of applications including non-destructive examination, medical imaging, military, and security purposes. Embodiments can provide an improved x-ray backscatter technology, and can provide a technique to speed up the creation of images from existing x-ray backscatter technology.

Applications of embodiments of the present invention include, but are not limited to scanner/imaging systems for detecting flaws and defects in materials and structures, scanners for detecting target objects and/or foreign object debris (FOD) inside of walls and structures, devices for security purposes to identify objects hidden in walls, containers or on individuals, portal scanning, law enforcement and Homeland Security applications, and medical imaging.

Advantageously, certain embodiments of the invention can significantly improve imaging speed. In addition, by using image reconstruction, three-dimensional images can be readily provided.

Figure 1B:
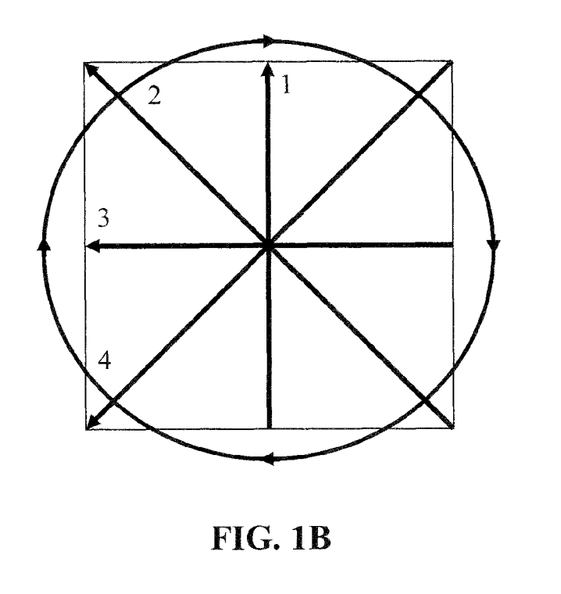
FIG. 1B shows a method of fan beam scanning according to an embodiment of the present invention.

Specific embodiments of the subject method differ from Radiography by Selective Detection (RSD) primarily in the method of image acquisition. A fan beam aperture can be used rather than a pencil beam. Embodiments of the subject invention can gather discrete data over the desired area, utilizing rotational motion, as shown for example in FIG. 1B. Referring to FIG. 1B, a fan beam extending for at least a portion, and preferably the entire, width from the left edge of the field of view to the right edge of the field of view is scanned along vector 1 from the bottom of the field of view to the top of the field of view. The fan beam can then be rotated and then scanned along vector 2 from the bottom right corner of the field of view to the upper left corner of the field of view, then scanned along vector 3 from the right of the field of view to the left of the field of view, and finally scanned along vector 4 from the upper right corner of the field of view to the lower left corner of the field of view. Of course, the directions of one or more of the vectors 1, 2, 3, and 4, can be reversed and the beam scanned in the opposite direction, the scans can be done as partial scans of the vectors, the order of the scans can be changed, the number of scans can be increased or decreased, and the angles between the vectors can be modified such that the vectors are not symmetrically distributed. The width of the fan beam can set a limit on the resolution of the image. The aspect ratio, i.e., the ratio of the length to the width of the beam, can impact the amount of time that can be saved versus pencil beam scanning. The detector detecting the backscattered radiation can be gated at certain intervals over each scan with the detected backscattered radiation put in bins corresponding to the portion of the object scanned during the time interval for the bin. The rate of scanning can be constant or can vary depending on the application. A non symmetrical distribution of the scanning vectors can allow particular portions of the field of view to be emphasized and the resolution of certain portions of the field of view to be increased or decreased.

Figure 4:
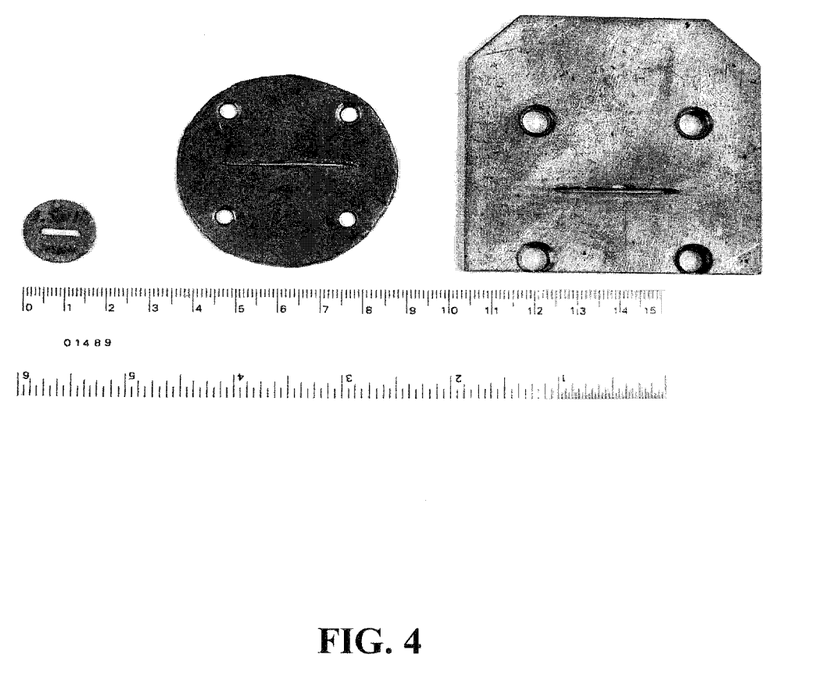
FIG. 4 shows fan beam slit apertures according to specific embodiments of the present invention.

Using rotational motion to gather the data is in contrast to the strictly Cartesian rastering movement shown in FIG. 1A. Fan beam scanning can provide several advantages over the pencil-beam scanning method. The use of varying shaped beams, such as oval, trapezoidal, or other non-rectangular shapes can allow adjustment of the resolution in portions of the field of view. In a specific embodiment, at least two fan beam scans are performed corresponding to vector at an angle to each other. In a further specific embodiment, the vectors for the two fan beam scans are at a 90 degree angle to each other. In further embodiments n scans are performed having vector at 180/n degree increments with respect to each other. Of course the angles between nearest neighbor vectors do not have to be the same. In a preferred embodiment, the aspect ratio of the fan beam, i.e., the ratio of the length to the width is at least 5. In further embodiments the aspect ratio can be at least 10, at least 30 (as shown in FIG. 4), at least 100, at least 1,000, at least 10,000, and at least 100,000. For an aspect ratio of 100,000, a field of view of 100 meters can be scanned by a beam 100 meters long and 1 mm wide, where such scanning could occur from, for example, a plane or helicopter.

According to an embodiment of the present invention, the scanning speed can be significantly increased by utilizing a line instead of a spot for illumination. The fan beam can create a higher intensity backscatter field, which allows the scanning speed to increase. In an embodiment, the total amount of motion can be decreased, because back-projection or algebraic reconstruction can be used generate and interpolate the image. Of course the scan speed can influence contrast. The data collected in a certain bin during the fan beam scan only provides one dimensional data, where combining the data from two scans at the portion of the field of view that the two scans intersect can provide two-dimensional data, and the data from all of the scans can provide pixel values at pixels on the field of view where scans intersect.

Figure 2A:
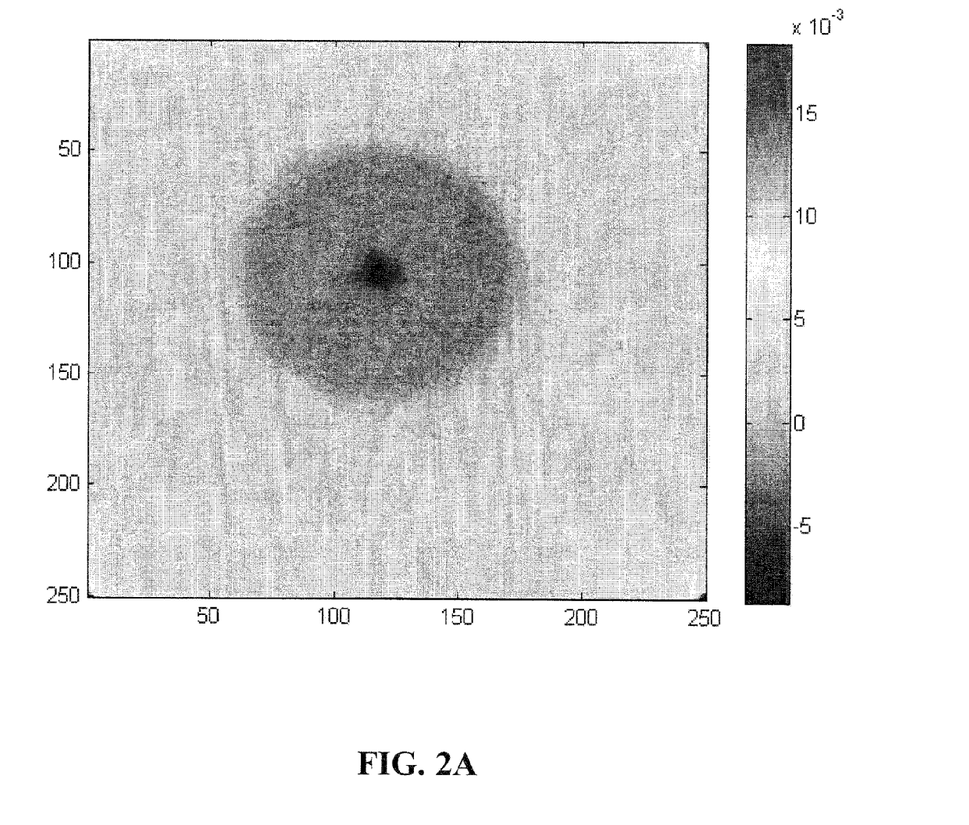
FIGS. 2A-2B show a surface scan image of a dime achieved according to an embodiment of the present invention.
Figure 2B:
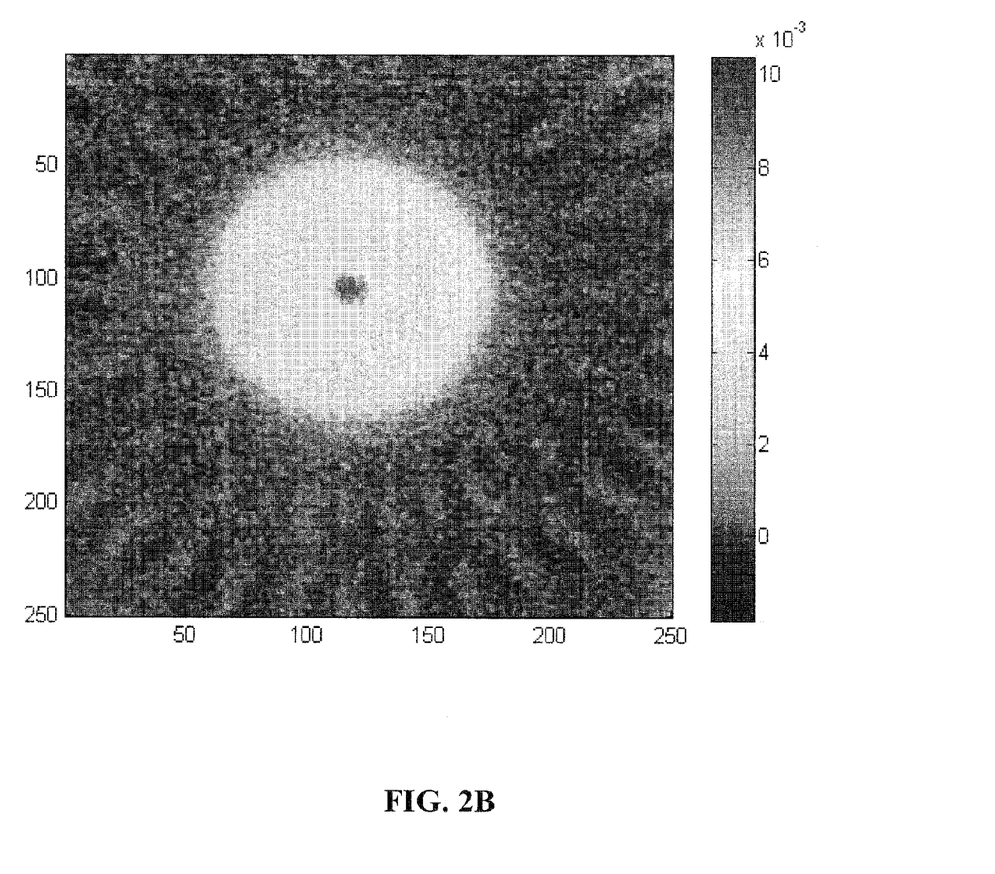
Figure 3A:
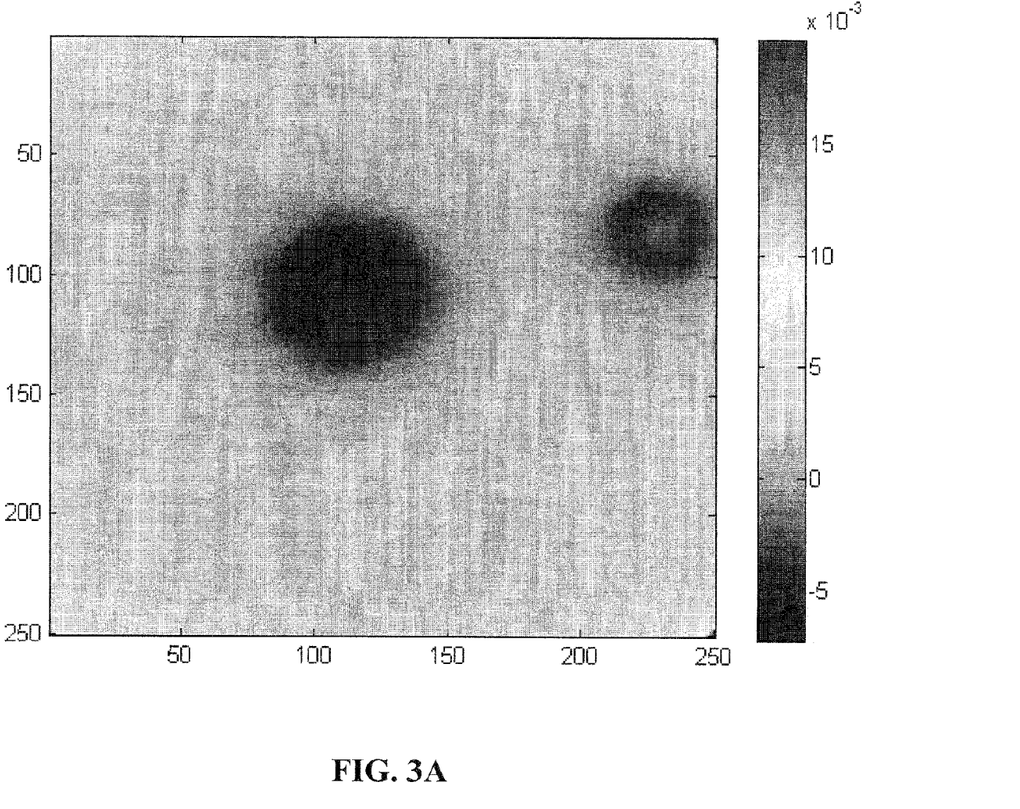
FIGS. 3A-3B show a surface scan image of a dime and a nut achieved according to an embodiment of the present invention.
Figure 3B:
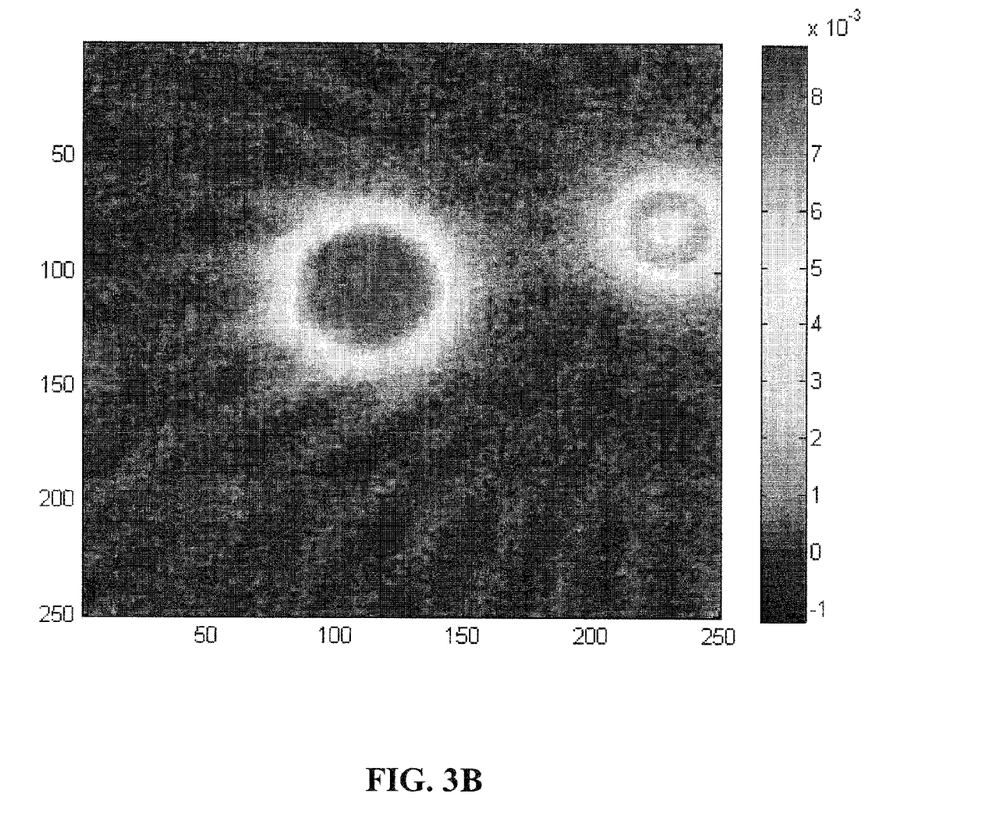

FIGS. 2A and 2B show the image from a backscatter surface scan of a dime. FIGS. 3A and 3B show the image from a backscatter surface scan of a centered dime and an off-centered nut. Both the dime and the nut are seen clearly, as is the hole in the nut. For both of these scans, 10 degree increments were used for the fan beam rotational movement. In both FIGS. 2A-2B and FIGS. 3A-3B, the area scanned was 100 mm×100 mm and the only difference between the left and right images in both of these two figures is contrast adjustment. The images in FIGS. 2A-2B and 3A-3B were constructed from the data taken via fan beam scans and reconstructed using a back projection technique used for CT image reconstruction. FIG. 4 shows three fan beam slit apertures.

Figure 5A:
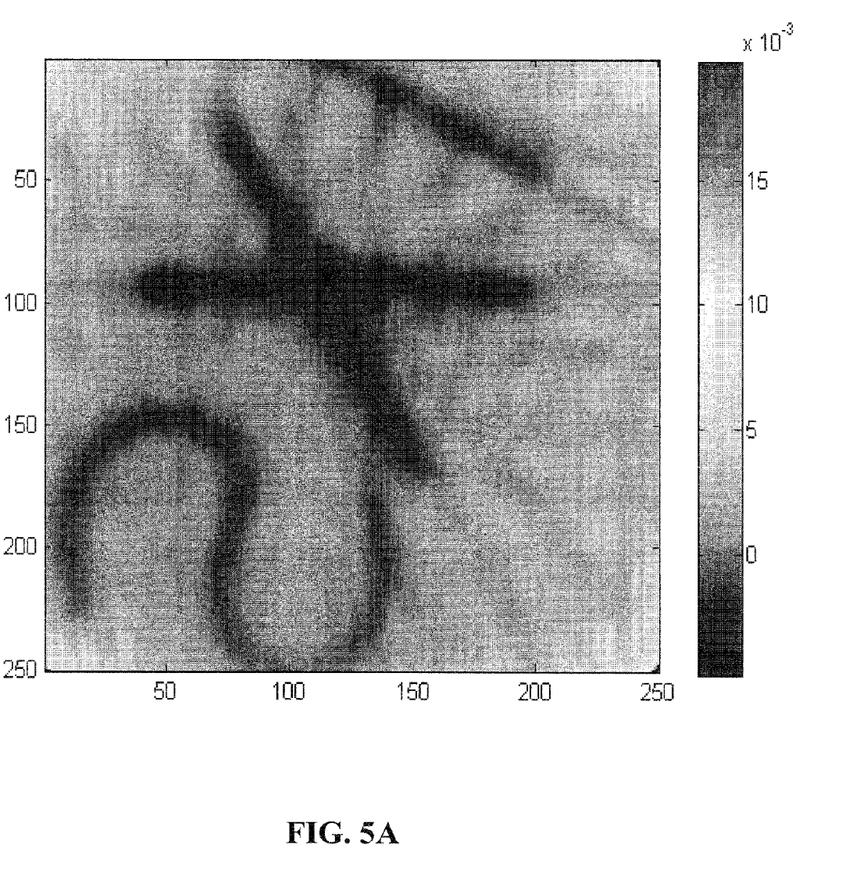
FIGS. 5A-5B show a surface scan image of lead letters on a nylon backing achieved utilizing an embodiment of the present invention.
Figure 5B:
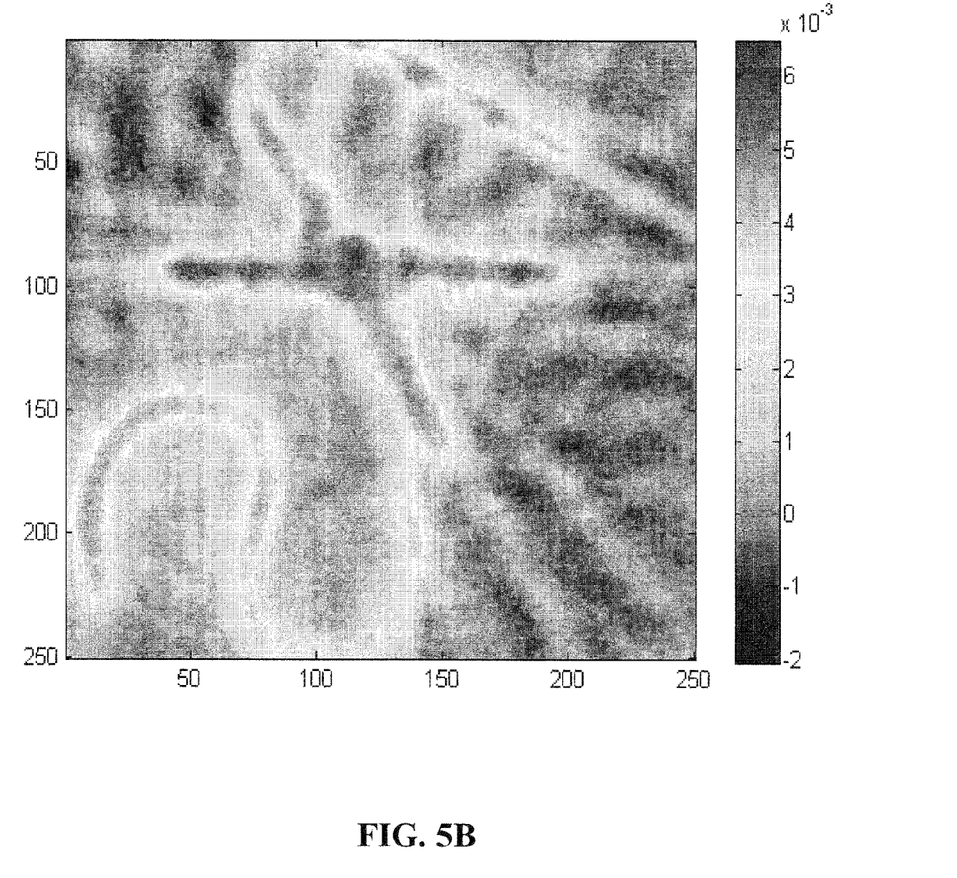
Figure 6:
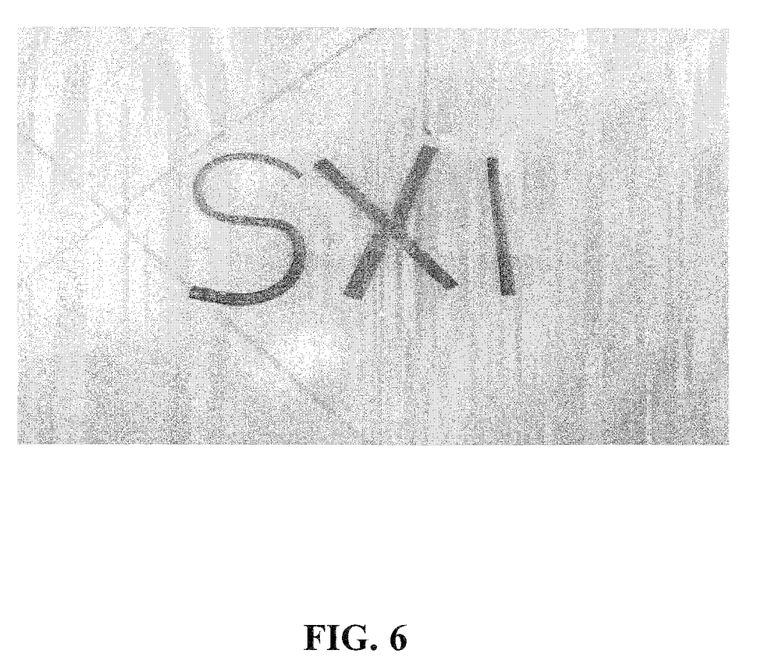
FIG. 6 shows a photograph of lead letters on a nylon backing imaged utilizing an embodiment of the present invention.

The fan beam aperture on the left was used in an initial experiment, the fan beam aperture in the center was used to obtain the results presented in FIGS. 2A-2B, 3A-3B, and 5A-5B, and the fan beam aperture on the right is a further embodiment. FIGS. 5A and 5B show the CIBR image from a backscatter surface scan of lead letters on a nylon backing. FIG. 6 shows a photograph of the lead letters on the nylon that were imaged in FIGS. 5A and 5B. The area scanned was 100 mm×100 mm and the only difference between the image in FIG. 5A and the image in FIG. 5B is contrast adjustment.

Tests implemented in accordance with embodiments of the invention using a fan beam aperture rotated during illumination have shown the ability to generate high-complexity images utilizing high-contrast objects at speeds greater than 3 times faster than current RSD scanning capabilities. Other means to rotate the fan beam can be used, including the combination of the x-ray head and slit aperture and/or the slit aperture. Of course, if the fan beam exits the radiation source, then rotation of the radiation source head rotates the fan beam. Further, the x-ray generator can be rocked back and forth in a direction perpendicular to the length of the fan beam in combination with rotation of the collimator. These images have been generated utilizing image reconstruction methods designed for computed tomography (CT) systems, which do not correlate directly to the method of scanning in accordance with embodiments of the subject method. In further embodiments, image reconstruction methods specifically geared to CIBR can be utilized. When reconstruction techniques directed to the embodiments implemented are used, image acquisition time can be further decreased and image quality can be improved. Image reconstruction methods directed to specific embodiments of the subject technique can provide three-dimensional backscatter images.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. A method of imaging, comprising:
   a. illuminating an object with a fan beam of radiation, wherein the fan beam of radiation has a length to width aspect ratio of at least 5;
   b. receiving back scattered radiation from the object;
   c. rotating the fan beam of radiation with respect to the object, wherein the fan beam of radiation is rotated about an axis that is perpendicular to the length of the fan beam of radiation and perpendicular to the width of the fan beam of radiation;
   d. re-illuminating the object with the fan beam of radiation;
   e. receiving additional back scattered radiation from the object;
   f. reconstructing an image of at least a portion of the object from the received back scattered radiation and the received additional back scattered radiation.

2. The method according to claim 1, wherein illuminating the object with a fan beam of radiation comprises scanning the fan beam of radiation across the object in a direction perpendicular to the length of the fan beam.

3. The method according to claim 2, wherein the aspect ratio is at least 10.

4. The method according to claim 2, wherein the aspect ratio is at least 30.

5. The method according to claim 2, wherein the aspect ratio is at least 100.

6. The method according to claim 2, wherein the aspect ratio is at least 1,000.

7. The method according to claim 2, wherein the aspect ratio is at least 10,000.

8. The method according to claim 2, wherein the aspect ratio is at least 100,000.

9. The method according to claim 1, wherein the fan beam of radiation is a fan beam of x-ray radiation.

10. The method according to claim 1, wherein the fan beam of radiation is a fan beam of penetrating radiation.

11. The method according to claim 1, wherein the fan beam of radiation is formed by passing radiation through a slit aperture.

12. The method according to claim 11, wherein the slit aperture is substantially rectangular-shaped.

13. The method according to claim 11, wherein the slit aperture is positioned on an x-ray head, wherein rotating the fan beam of radiation comprises rotating an x-ray head-slit aperture combination.

14. The method according to claim 11, wherein the slit aperture is positioned on an x-ray head, wherein rotating the fan beam of radiation comprises rotating the slit aperture.

15. The method according to claim 1, further comprising, after e, repeating c, d, and e, n–2 times prior to f, wherein rotating the fan beam of radiation comprises rotating the fan beam of radiation by 180°/n each time.

16. The method according to claim 1, wherein the back scattered radiation and the additional back scattered radiation are received on the same side of the object as the fan beam of radiation illuminates the object.

17. The method according to claim 1, wherein reconstructing the image comprises reconstructing the image via back-projection reconstruction.

18. The method according to claim 1, wherein reconstructing the image comprises reconstructing the image via algebraic reconstruction.

19. The method according to claim 1, wherein the width of the fan beam of radiation is less than or equal to 1 mm.

20. The method according to claim 1, wherein the radiation is selected from the group consisting of the following: gamma rays, electrons, and neutrons.

21. The method according to claim 1, wherein rotating the fan beam of radiation with respect to the object comprises rotating the fan beam of radiation.

22. The method according to claim 1, wherein rotating the fan beam of radiation with respect to the object comprises rotating the object.

23. The method according to claim 1, wherein reconstructing an image of at least a portion of the object comprises reconstructing a 2D image of at least a portion of the object.

24. The method according to claim 1, wherein reconstructing an image of at least a portion of the object comprises reconstructing a 3D image of at least a portion of the object.

25. An apparatus for imaging, comprising:
a radiation source, wherein the radiation source directs a fan beam of radiation at an object to be imaged, wherein the fan beam of radiation is rotated with respect to the object, wherein the fan beam of radiation has a length to width aspect ratio of at least 5, wherein the fan beam of radiation is rotated about an axis that is perpendicular to the length of the fan beam of radiation and perpendicular to the width of the fan beam of radiation;
a detector positioned to detect back scattered radiation from the object;
a processor, wherein upon receipt of detected back scattered radiation from the object corresponding to at least two rotation positions of the fan beam of radiation with respect to the object, the processor reconstructs an image of at least a portion of the object from the detected back scattered radiation from the object corresponding to the at least two rotation positions of the fan beam of radiation with respect to the object.

26. The apparatus according to claim 25, wherein the fan beam of radiation is scanned across the object in a direction perpendicular to the length of the fan beam.

27. The apparatus according to claim 26 wherein the aspect ratio is at least 10.

28. The apparatus according to claim 26 wherein the aspect ratio is at least 30.

29. The apparatus according to claim 26 wherein the aspect ratio is at least 100.

30. The apparatus according to claim 26 wherein the aspect ratio is at least 1,000.

31. The apparatus according to claim 26 wherein the aspect ratio is at least 10,000.

32. The apparatus according to claim 26, wherein the aspect ratio is at least 100,000.

33. The apparatus according to claim 25, wherein the fan beam of radiation is a fan beam of x-ray radiation.

34. The apparatus according to claim 25, wherein the fan beam of radiation is a fan beam of penetrating radiation.

35. The apparatus according to claim 25, wherein the fan beam of radiation is formed by passing radiation through a slit aperture.

36. The apparatus according to claim 35, wherein the slit aperture is substantially rectangular-shaped.

37. The apparatus according to claim 35, wherein the slit aperture is positioned on an x-ray head, wherein rotation of the fan beam of radiation with respect to the object comprises rotation of an x-ray head-slit aperture combination.

38. The apparatus according to claim 35, wherein the slit aperture is positioned on an x-ray head, wherein rotation of the fan beam of radiation with respect to the object comprises rotation of the slit aperture.

39. The apparatus according to claim 25, wherein the at least two rotation positions are n rotation positions, wherein the fan beam of radiation is rotated about the axis that is perpendicular to the length of the fan beam of radiation and perpendicular to the width of the fan beam of radiation by 180°/n between each of the n rotation positions.

40. The apparatus according to claim 25, wherein the detected back scattered radiation corresponding to the at least two rotation positions of the fan beam of radiation with respect to the object is received on the same side of the object as the radiation source directed the fan beam of radiation at the object to be imaged.

41. The apparatus according to claim 25, wherein the processor reconstructs the image of at least a portion of the object via back-projection reconstruction.

42. The apparatus according to claim 25, wherein the processor reconstructs the image of at least a portion of the object via algebraic reconstruction.

43. The apparatus according to claim 25, wherein the width of the fan beam of radiation is less than or equal to 1mm.

44. The apparatus according to claim 25, wherein the radiation is selected from the group consisting of the following: gamma rays, electrons, and neutrons.

45. The apparatus according to claim 25, wherein rotation of the fan beam of radiation with respect to the object comprises rotation of the fan beam of radiation.

46. The apparatus according to claim 25, wherein rotation of the fan beam of radiation with respect to the object comprises rotation of the object.

47. The apparatus according to claim 25, wherein the processor reconstructs a 2D image of at least a portion of the object.

48. The apparatus according to claim 25, wherein the processor reconstructs a 3D image of at least a portion of the object.

* * * * *